United States Patent [19]

Santroch et al.

[11] Patent Number: 4,515,949

[45] Date of Patent: May 7, 1985

[54] [2-(1H-INDOL-1-YL)ETHYL]-2-PIPERAZINE AND PYRIDO[1,2-A]INDOL-9-ONE AS INTERMEDIATES FOR PYRAZINO(2,3-3,4)PYRIDO(1,2-A) INDOLES WHICH ARE USEFUL FOR TREATING HYPERTENSION IN MAMMALS

[75] Inventors: George Santroch, San Francisco, Calif.; Ivo Jirkovsky, Montreal, Canada

[73] Assignee: American Home Products Corporation, New York, N.Y.

[21] Appl. No.: 583,908

[22] Filed: Feb. 27, 1984
(Under 37 CFR 1.47)

Related U.S. Application Data

[62] Division of Ser. No. 461,095, Jan. 26, 1983.

[51] Int. Cl.³ .................. C07D 241/36; C07D 403/00; C07D 451/00; A61K 31/495
[52] U.S. Cl. .................................. 544/343; 544/373; 546/94
[58] Field of Search .......................... 544/373; 546/94

[56] References Cited

U.S. PATENT DOCUMENTS 4,482,714 11/1984 Santroch et al. .................. 544/343

OTHER PUBLICATIONS

Winterfeldt et al., Chem. Abst. 74:111850z (1971).
Coffen et al., Chem. Abst. 81:78127p (1974).
Winterfeldt et al., Chem. Ber. 1971, 104(3), 802–807.
Coffen et al., J. A. C. S. 1974, 96(12), 3966–3973.

Primary Examiner—Donald G. Daus
Assistant Examiner—Cecilia Shen

[57] ABSTRACT

A compound of the formula

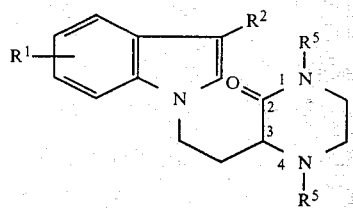

in which
$R^1$ is hydrogen, halogen, lower alkyl, lower alkoxy or trifluoromethyl;
$R^2$ is hydrogen or lower alkyl having one to three carbon atoms; and
$R^5$ is benzyl or lower alkyl;

and a compound of the formula

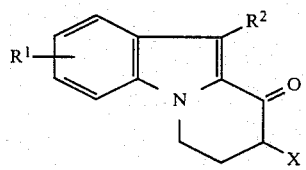

in which
$R^1$ is hydrogen, halogen, lower alkyl, lower alkoxy or trifluoromethyl;
$R^2$ is hydrogen or lower alkyl having one to three carbon atoms; and
X is bromo or chloro, or hydrogen;

as intermediates for pyrazino(2,3-3,4) pyrido (1,2-a) indoles which are useful for treating hypertension in mammals.

6 Claims, No Drawings

[2-(1H-INDOL-1-YL)ETHYL]-2-PIPERAZINE AND PYRIDO[1,2-A]INDOL-9-ONE AS INTERMEDIATES FOR PYRAZINO(2,3-3,4)PYRIDO(1,2-A) INDOLES WHICH ARE USEFUL FOR TREATING HYPERTENSION IN MAMMALS

BACKGROUND OF THE INVENTION

This is a division of application Ser. No. 461,095, filed Jan. 26, 1983.

This invention relates to novel pyrazino[2',3'-3,4]pyrido[1,2-a]-indole derivatives, to therapeutically acceptable acid addition salts thereof, to processes for their preparation, to methods of using the derivatives and to pharmaceutical compositions of the derivatives. These derivatives are useful for treating hypertension in a mammal.

SUMMARY OF THE INVENTION

The compounds of this invention are represented by formula I

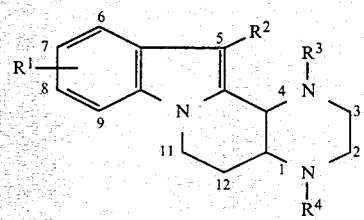

in which $R^1$ is hydrogen, halogen, lower alkyl, lower alkoxy or trifluoromethyl; $R^2$ is hydrogen or lower alkyl having one to three carbon atoms; and $R^3$ and $R^4$ each is hydrogen, lower alkyl, lower alkenyl, lower alkynyl, cyclo(lower)alkyl, lower alkanoyl, hydroxy(lower)alkyl, lower alkoxycarbonyl(lower)alkyl, phenyl(lower)alkyl or phenoxy(lower)alkyl; or a therapeutically acceptable acid addition salt thereof.

The above compounds of formula I include the trans and cis compounds of formula Ia and Ib, respectively

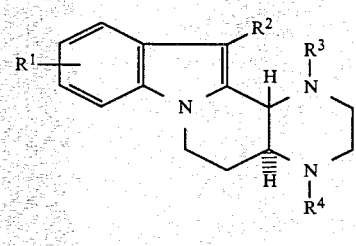

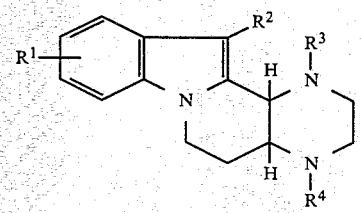

in which $R^1$, $R^2$, $R^3$ and $R^4$ are as defined herein.

A preferred group of compounds of this invention is represented by formula I in which $R^1$ is hydrogen or bromo; $R^2$ is methyl; $R^3$ and $R^4$ each independently is hydrogen, lower alkyl, lower alkynyl, lower alkanoyl, hydroxy(lower)alkyl, lower alkoxycarbonyl(lower)alkyl, or phenoxy(lower)alkyl; or a therapeutically acceptable acid addition salt thereof.

Another preferred group of compounds of this invention is represented by formula Ia in which $R^1$ is hydrogen or bromo; $R^2$ is methyl; $R^3$ is hydrogen, lower alkyl, lower alkanoyl, hydroxy(lower)alkyl or lower alkoxycarbonyl(lower)alkyl; and $R^4$ is hydrogen, lower alkyl, lower alkynyl, hydroxy(lower)alkyl or lower alkoxycarbonyl(lower)alkyl; or a therapeutically acceptable acid addition salt thereof.

A most preferred group of compounds of this invention is represented by formula Ia in which $R^1$ is hydrogen; $R^2$ is methyl; $R^3$ is hydrogen, lower alkyl or hydroxy(lower)alkyl; and $R^4$ is hydrogen, lower alkyl, lower alkynyl or hydroxy(lower)alkyl; or a therapeutically acceptable acid addition salt thereof.

The compounds of formula I or a therapeutically acceptable acid addition salt thereof can be prepared by selecting a process from the group of:

(a) cyclizing a compound of formula II

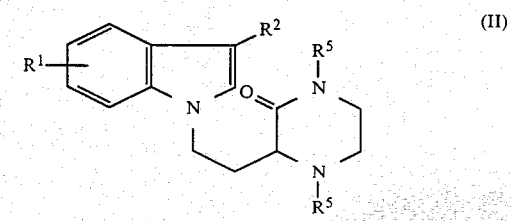

in which $R^1$ and $R^2$ are as defined herein, and $R^5$ is lower alkyl to obtain the corresponding compound of formula Ib in which $R^1$ and $R^2$ are as defined herein, and $R^3$ and $R^4$ are the same lower alkyl;

(b) hydrogenating a compound of formula III

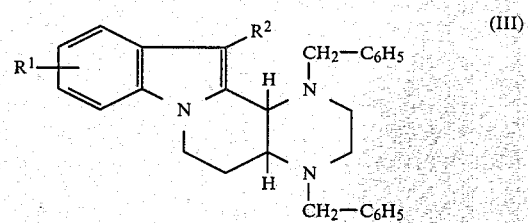

in which $R^1$ and $R^2$ are as defined herein to obtain the corresponding compound of formula Ib in which $R^1$ and $R^2$ are as defined herein, and $R^3$ and $R^4$ are hydrogen;

(c) condensing a compound of formula IV

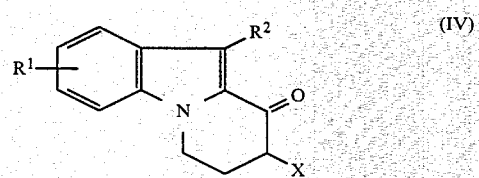

in which $R^1$ and $R^2$ are as defined herein and X is bromo or chloro with ethylenediamine and reducing the resulting intermediate to obtain the corresponding compound of formula Ia in which $R^1$ and $R^2$ are as defined herein, and $R^3$ and $R^4$ are hydrogen;

(d) subjecting a compound of formula I in which $R^1$ and $R^2$ are as defined herein, and $R^3$ and $R^4$ are hydrogen to alkylation, acylation and/or reduction in optional order and to the extent required to obtain the corresponding compound of formula I in which $R^1$ and $R^2$ are as defined herein, and $R^3$ and $R^4$ each is hydrogen, lower alkyl, lower alkenyl, lower alkynyl, cyclo(lower)alkyl, lower alkanoyl, hydroxy(lower)alkyl, lower alkoxycarbonyl(lower)alkyl, phenyl(lower)alkyl or phenoxy(lower)alkyl; and (e) reacting a compound of formula I in which $R^1$, $R^2$, $R^3$ and $R^4$ are as defined herein with a therapeutically acceptable acid to obtain the corresponding compound of formula I as the salt with the therapeutically acceptable acid.

A pharmaceutical composition is provided by combining the compound of formula I, or a therapeutically acceptable acid addition salt thereof, and a pharmaceutically acceptable carrier.

The compounds of this invention can be used to treat hypertension in a hypertensive mammal by administering to the mammal an effective antihypertensive amount of a compound of formula I or a therapeutically acceptable acid addition salt thereof optionally with a second antihypertensive agent.

DETAILED DESCRIPTION OF THE INVENTION

The term "lower alkyl" as used herein means straight and branched chain alkyl radicals containing from one to six carbon atoms, preferably one to four carbon atoms, and includes methyl, ethyl, propyl, 1-methylethyl, butyl, 1,1-dimethylethyl, pentyl and the like, unless stated otherwise.

The term "halo" as used herein means halo radicals and includes fluoro, chloro, bromo and iodo, unless stated otherwise.

The term "lower alkoxy" as used herein means straight chain alkoxy radicals containing from one to six carbon atoms and branched chain alkoxy radicals containing three to six carbon atoms and includes methoxy, ethoxy, 1-methylethoxy, butoxy, hexoxy and the like.

The term "lower alkanoyl" as used herein means straight chain 1-oxoalkyl radicals containing from two to six carbon atoms and branched chain 1-oxoalkyl radicals containing four to six carbon atoms and includes acetyl, 1-oxopropyl, 2-methyl-1-oxopropyl, 1-oxohexyl and the like.

The term "lower alkenyl" as used herein means straight chain alkenyl radicals containing from two to six carbon atoms and branched chain alkenyl radicals containing three to six carbon atoms and includes ethenyl, 2-methyl-2-propenyl, 4-hexenyl and the like.

The term "lower alkynyl" as used herein means straight chain alkynyl radicals containing from two to six carbon atoms and branched chain alkynyl radicals containing four to six carbon atoms and includes ethynyl, 2-propynyl, 1-methyl-2-propynyl, 3-hexynyl and the like.

The term "cyclo(lower)alkyl" as used herein means saturated cyclic hydrocarbon radicals containing from four to six carbon atoms and includes cyclobutyl, cyclopentyl and cyclohexyl.

The term "complex borohydride" as used herein means the metal borohydrides and includes, for example, sodium borohydride, sodium cyanoborohydride, potassium borohydride, lithium borohydride and zinc borohydride.

The term "complex metal hydride" as used herein means metal hydride reducing agents and includes, for example, lithium aluminum hydride, lithium aluminum hydride-aluminum chloride, diisobutylaluminum hydride, and sodium bis-(2-methoxyethoxy)aluminum hydride.

The term "lower alkanol" as used herein means both straight and branched chain alkanols containing from one to four carbon atoms and includes methanol, ethanol, 1-methylethanol, butanol and the like.

The term "organic proton acceptor" as used herein means the organic bases or amines, for instance, triethylamine, pyridine, N-ethylmorpholine, 1,5-diazabicyclo[4.3.0]non-5-ene and the like.

The term "inorganic proton acceptor" as used herein means the inorganic bases, preferably the alkali methyl hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined hereinabove.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanoldiethyl ether mixture.

These salts, when administered to a mammal, possess the same pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The antihypertensive effect of the compounds of formula I or a therapeutically acceptable acid addition salt thereof is demonstrated in standard pharmacological tests, for example, in tests conducted in the spontaneously hypertensive rate (SHR). The latter test method is as follows: Male rats, Okamoto-Aoki Strain, ranging in weight between 250–400 g were anesthetized with diethyl ether. Their left femoral arteries and veins were cannulated with polyethylene tubing of the appropriate size. Each animal was then enfolded in a rubber mesh jacket which was secured with 4 towel clamps. The animal was suspended via the towel clamps from a bar and allowed to recover from the anesthesia. The femorial arterial cannula was connected to a Stratham pressure transducer (Model P23, Gould Stratham Instruments, Hato Rey, Porto Rico), which in turn was attached to a polygraph for recording the mean arterial blood pressure and pulse rate. The pulse rate was considered to be the heart rate. The test compound was administered by gastric gavage in a volume of 5 ml/kg. Heart rate and blood pressure were noted at 5, 10, 15, 30, 45 and 60 minutes and hourly thereafter for a period of at least 4 hours after drug administration.

Using this method, the following representative compounds of formula I are effective for reducing the blood pressure (BP) in the spontaneously hypertensive rat (the amount of test compound and the reduction in BP are indicated in the parenthesis):

(4a,12a-cis)-1,4-diethyl-5-methyl-1,2,3,4,4a,11,12,12a-octahydropyrazino[2',3'-3,4]pyrido[1,2-a]indole dihydrochloride (described in Example 5, at a dose of 25 mg/kg of body weight caused a 20% decrease in mean BP at 1 hour), (4a,12a-trans)-5-methyl-1,2,3,4,4a,11,12,-12a-octahydropyrazino[2',3'-3,4]pyrido[1,2-a]indole maleate (described in Example 11, at a dose of 10 mg/kg of body weight caused a 19% decrease in BP at 4 hours), (4a,12a-trans)-7-bromo-1,4-diethyl-5-methyl-1,2,3,4,4a,11,12,12a-octahydropyrazino[2',3'-3,4]pyrido[1,2-a]indole hydrochloride (described in Example 12, at a dose of 10 mg/kg of body weight caused a 15% decrease in BP at 4 hours), 4a,12-a-trans)-1-(2-propynyl)-5-methyl-1,2,3,4,4a,11,12,12a-octahydropyrazino[2',3'-3,4]pyrido[1,2-a]indole dihydrochloride (described in Example 13, at a dose of 10 mg/kg of body weight caused a 14% decrease in BP at 4 hours), (4a,12a-trans)-1,4,5-trimethyl-1,2,3,4,4a,11,12,12a-octahydropyrazino[2',3'-3,4]pyrido[1,2-a]indole maleate (described in Example 14, at a dose of 10 mg/kg of body weight caused a 23% decrease in BP at 4 hours), (4a,12a-trans)-5-methyl-1,2,3,4,4a,11,12,12a-octahydropyrazino[2',3'-3,4]pyrido[1,2-a]indole-1,4-diethanol dihydrochloride (described in Example 15, at a dose of 10 mg/kg of body weight caused a 34% decrease in BP at 1 hour), (4a,12a-trans)-1-ethyl-5-methyl-4-propyl-1,2,3,4,4a,11,12,12a-octahydropyrazino[2',3'-3,4]pyrido[1,2-a]indole hydrobromide (described in Example 17, at a dose of 10 mg/kg of body weight caused a 42% decrease in BP at 4 hours), (4a,12a-trans)-4-butyl-1-ethyl-5-methyl-1,2,3,4,4a,11,12,12a-octahydropyrazino[2',3'-3,4]pyrido[1,2-a]indole dihydrochloride (described in Example 17, at a dose of 10 mg/kg of body weight caused a 36% decrease in BP at 4 hours), and (4a,12a-trans)-4-ethyl-5-methyl-(1-methylethyl)-1,2,3,4,4a,11,12,12a-octahydropyrazino[2',3'-3,4]pyrido[1,2-a]indole dihydrobromide (described in Example 17, at a dose of 10 mg/kg caused a 43% decrease in BP at 4 hours).

The compounds of formula I of this invention are used alone or in combination with pharmacologically acceptable carriers, the proportion of which is determined by the solubility and chemical nature of the compound, chosen route of administration and standard biological practice. For example, they are administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as antihypertensive agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective antihypertensive amount of the compounds for oral administration can usually range from about 0.05 to 100 mg per kilogram body weight per day in single or divided doses although as aforementioned variations will occur. However, a dosage level that is in the range of from about 0.1 to 50 mg per kilogram body weight per day in single or divided doses is employed most desirably for oral administration in order to achieve effective results.

The compounds of formula I also can be used to produce beneficial effects in the treatment of hypertension, peripheral and cerebral vascular diseases and related disorders when combined with a second therapeutic agent comprising a therapeutically effective amount of a diuretic and/or antihypertensive agent commonly used in antihypertensive therapy. Such diuretic and/or antihypertensive therapeutic agents include, for example, the thiazide diuretics for instance, chlorothiazide or hydrochlorothiazide; mineralocorticoid antagonizing diuretic agents, e.g., spironolactone; and other diuretics such as triameterene and furosemide. Examples of still other suitable antihypertensive agents are prazosine, hydralazine and centrally active antihypertensive agents such as methyldopa, clonidine, and reserpine; as well as the β-adrenergic blocking agents, for instance, propranolol. The compound of formula I can be administered sequentially or simultaneously with the antihypertensive and/or diuretic agent. Preferred antihypertensive and/or diuretic therapeutic agents are the antihypertensive agents such as the thiazides, mineralocorticold antagonizing diuretic agents and the β-adrenergic blocking agents. A combination of the foregoing antihypertensive agents are well known in the art; for instance, "Physician Desk Reference", 33 ed., Medical Economics Co., Oradell, N.J., U.S.A., 1979. For example, propranolol is administered daily to humans in a range of 80 to 640 mg, usually in the form of unit doses of 10, 20, 40 or 80 mg. When used in combination, the compound of formula I is administered as described previously.

The compounds of formula I are prepared in the following manner.

Reaction scheme 1 illustrates a method for preparing some of the compounds of formula Ib.

the condensation, toluene is preferred. The condensation is usually conducted at about 100° to 120° C. for about 15 to 30 hours.

In order to form the indole ring system, the compound of formula VIII in which $R^1$, $R^2$ and $R^5$ are as defined herein is oxidized with a mixture of manganese

REACTION SCHEME 1

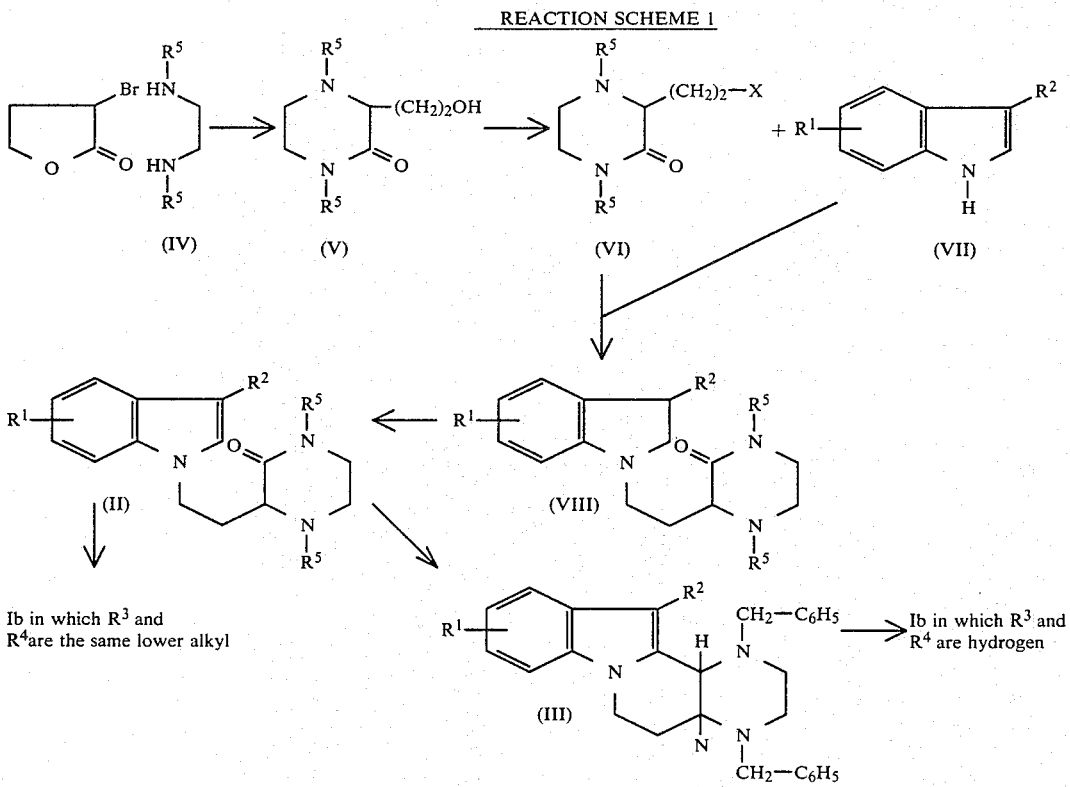

With reference to reaction scheme 1, bromobutyrolactone is condensed with an ethylenediamine derivative of formula IV in which $R^5$ is benzyl or lower alkyl to obtain the corresponding piperazine of formula V in which $R^5$ is as defined herein. Preferred conditions for the condensation involve reacting together about equivalent amounts of bromobutyrolactone and the compound of formula IV in the presence of an equivalent amount of a proton acceptor, preferably triethylamine, in an inert organic solvent, preferably tetrahydrofuran, at about 60° to 70° C. for about 15 to 30 hours.

Reaction of the piperazine of formula V in which $R^5$ is as defined herein with about 10 to 25 molar equivalents of thionyl chloride or bromide gives the corresponding piperazine of formula VI in which $R^5$ is as defined herein and X is bromo or chloro. A suitable solvent is methylene chloride and the reaction is conducted at about 0° to 20° C. for about 15 minutes to two hours.

Condensation of the piperazine of formula VI in which $R^5$ and X are as defined herein with a dihydroindole of formula VII in which $R^1$ and $R^2$ are as defined herein gives the corresponding compound of formula VIII in which $R^1$, $R^2$ and $R^5$ are as defined herein. A useful method of preparing the dihydroindoles of formula VII from the corresponding indole is described by A. Smith and J. H. P. Utley, Chem. Commun., 427 (1965). Preferably about 1.5 molar equivalents of the piperazine of formula VI is used with respect to the dihydroindole of formula VII. For the inert solvent in dioxide and palladium on charcoal to obtain the corresponding compound of formula II in which $R^1$, $R^2$ and $R^5$ are as defined herein. Preferably about equal parts by weight of manganese dioxide and about one tenth part by weight of 5 percent palladium on charcoal is used. The oxidation is maintained at about 125° to 150° C. for about 15 to 30 hours in an inert organic solvent, preferably xylene.

Cyclodehydration of the compound of formula II in which $R^1$ and $R^2$ are as defined herein and $R^5$ is lower alkyl with phosphorus oxychloride followed by reduction of the resulting intermediate gives the corresponding compound of formula Ib in which $R^1$ and $R^2$ are as defined herein, and $R^3$ and $R^4$ are the same lower alkyl. In the cyclodehydration, an excess of phosphorus oxychloride is used or usually phosphorus oxychloride also acts as the solvent for the cyclodehydration. The cyclodehydration is conducted at about 90° to 110° C. for about two to ten hours. The intermediate obtained from the cyclodehydration is immediately reduced with an excess of sodium in a lower alkanol, preferably ethanol, at about 15° to 25° C. for about 15 minutes to one hour.

Similarly, cyclodehydration of the compound of formula II in which $R^1$ and $R^2$ are as defined herein and $R^5$ is benzyl followed by reduction of the resulting intermediate gives the corresponding compound of formula III in which $R^1$ and $R^2$ are as defined herein.

Hydrogenation of the compound of formula III in which $R^1$ and $R^2$ are as defined herein, preferably in the presence of palladium on carbon in a lower alkanol, affords the corresponding compound of formula Ib in which $R^1$ and $R^2$ are as defined herein, and $R^3$ and $R^4$ are hydrogen.

Reaction scheme 2 illustrates a method for preparing some of the compounds of formula Ia.

REACTION SCHEME 2

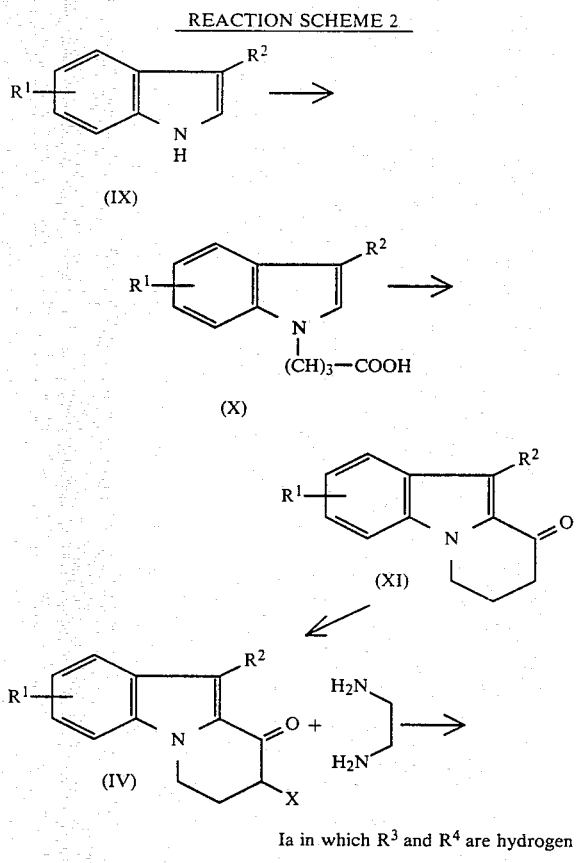

Ia in which $R^3$ and $R^4$ are hydrogen

With reference to reaction scheme 2, an indole of formula IX in which $R^1$ and $R^2$ are as defined herein, is condensed with butyrolactone to obtain the corresponding acid of formula X in which $R^1$ and $R^2$ are as defined herein. In this condensation, the indole of formula IX is first reacted with about one molar equivalent of sodium hydride at about 100° C. to generate the anion of the compound of formula IX. A solution of the anion in an inert organic solvent, preferably dimethylformamide, is mixed with about two molar equivalents of butyrolactone. The resulting solution is maintained at about 130° to 160° C. for about five to ten hours, and the corresponding acid of formula X is isolated.

Dehydrative cyclization of the acid of formula X in which $R^1$ and $R^2$ are as defined herein gives the corresponding tricyclic ketone of formula XI in which $R^1$ and $R^2$ are as defined herein. Preferred conditions for the cyclization involve reacting the acid of formula X with an excess of a dehydrating agent, preferably polyphosphoric acid, which can also act as the solvent, at about 80° to 120° C. for about 30 minutes to 5 hours.

A number of methods can be used to convert the tricyclic ketone of formula XI in which $R^1$ and $R^2$ are as defined herein to the halo compound of formula IV in which $R^1$ and $R^2$ are as defined herein and X is bromo or chloro. Examples of such methods include use of bromine or chlorine in various inert organic solvents, for example, diethyl ether, chloroform, methylene chloride and acetic acid, at various temperatures (i.e. −78° to 20° C.); N-bromosuccinimide or N-chlorosuccinimide in an inert organic solvent at 0° to 30° C.; dioxane dibromide; pyridinium hydrobromide perbromide; trimethylphenylammonium tribromide; and a mixture of trimethylphenylammonium tribromide and hydrogen bromide. For the subsequent condensation, the compounds of formula IV in which $R^1$ and $R^2$ are as defined herein an X is bromo are preferred. The preferred method of preparing the latter compounds of formula IV in which X is bromo involves reacting, in the dark, the compound of formula XI with about one molar equivalent of trimethylphenylammonium tribromide in an inert organic solvent, preferably methylene chloride, at about 10° to 30° C. for about 20 to 40 hours.

Condensation of the compound of formula IV in which $R^1$, $R^2$ and X are as defined herein with ethylenediamine and followed by reduction of the resulting intermediate gives the corresponding compound of formula Ia in which $R^1$ and $R^2$ are as defined herein, and $R^3$ and $R^4$ are hydrogen. In the condensation, about two to ten molar equivalents of ethylenediamine are required and an inert organic solvent, preferably dioxane, is used to dissolve the reactants. The condenation reaction is maintained at about 15° to 30° C. for about 15 to 30 hours. Preferably without isolating the condensation product, the condensation reaction mixture is treated with a complex borohydride reducing agent, preferably sodium borohydride, in order to reduce the product of the condensation. For the reduction, usually the condensation reaction mixture is diluted with a lower alkanol, preferably methanol, and a small amount of water, and the reduction reaction is maintained at about 10° to 30° C. for about one to five hours.

If desired, the compound of formula I (includes compounds of formulae Ia and Ib) in which $R^1$ and $R^2$ are as defined herein, and $R^3$ and $R^4$ are hydrogen can be reacted with a lower alkyl, lower alkenyl, lower alkynyl, cyclo(lower)alkyl, lower alkanoyl, lower alkoxycarbonyl(lower)alkyl, phenyl(lower)alkyl or phenoxy(lower)alkyl halide wherein the halide is selected from bromo, chloro or iodo in the presence of a proton acceptor to obtain the corresponding compound of formula I in which $R^1$ and $R^2$ are as defined herein, and $R^3$ and $R^4$ each is hydrogen, lower alkyl, lower alkenyl, lower alkynyl, cyclo(lower)alkyl, lower alkanoyl, lower alkoxycarbonyl(lower)alkyl, phenyl(lower)alkyl or phenoxy(lower)alkyl. Preferred proton acceptors include potassium carbonate and triethylamine, and preferred solvents are benzene, acetonitrile, dimethylformamide and methylene chloride. The amount of halide alkylating agent can vary from about 1.1 to 1.5 molar equivalents if monosubstitution is desired and from about three to ten molar equivalents if disubstitution is desired. The reaction conditions can also vary; usually a temperature of about 10° to 50° C. for about one to ten hours will produce monosubstitution and a temperature of about 20° to 120° C. for about 6 to 72 hours will give disubstitution. A monosubstituted compound of formula I, i.e. $R^3$ or $R^4$ is hydrogen, can then be substituted in the above manner to obtain the corresponding compound of formula I in which $R^1$ and $R^2$ are as defined herein, and $R^3$ and $R^4$ are different and are selected from lower alkyl, lower alkenyl, lower alkynyl, cyclo(lower)alkyl, lower alkanoyl, lower alkoxycarbonyl(lower)alkyl, phenyl(lower)alkyl and phenoxy(lower)alkyl.

A preferred method for preparing the compound of formula I in which $R^1$ and $R^2$ are as defined herein, and $R^3$ and $R^4$ are methyl involves reacting the hydrochloride salt of the corresponding compound of formula I in which $R^1$ and $R^2$ are as defined herein, and $R^3$ and $R^4$ are hydrogen with aqueous formaldehyde at about 10° to 30° C. for about one to ten hours. The resulting intermediate is then reduced by treating the reaction mixture with the reducing agent, sodium cyanoborohydride, at about 10° to 30° C. for about 15 to 30 hours.

Usually, the above alkylation type reactions will preferentially first take place at one of the secondary nitrogen positions, for example, in the compound of formula Ia, the secondary nitrogen at position 1 of the ring system is the more reactive. If it is desired that the alkylation type reaction take place at the less reactive secondary nitrogen, the more reactive nitrogen can be blocked by an easily removable blocking group. Such a blocking group is introduced by reaction with about one molar equivalent of benzoyl chloride. After the desired alkylation type reaction is conducted at the other secondary position, the benzoyl blocking group is removed under alkaline hydrolysis.

If desired, the compound of formula I in which $R^1$ and $R^2$ are as defined herein, and $R^3$ and/or $R^4$ is lower alkoxycarbonyl(lower)alkyl can be reduced with a complex metal hydride reducing agent to obtain the corresponding compound of formula I in which $R^1$ and $R^2$ are as defined herein, and $R^3$ and/or $R^4$ is hydroxy(lower)alkyl. For the reduction, about four to six molar equivalents of lithium aluminum hydride, as the preferred complex metal hydride reducing agent, is used and the reduction is conducted in an inert organic solvent, preferably diethyl ether. The reduction is maintained at about 30° to 50° C. for about 10 to 20 hours.

If desired, some of the trans compounds of formula Ia can be isomerized to the corresponding cis compounds of formula Ib. Most of the trans compounds of formula Ia in which $R^3$ and $R^4$ are not hydrogen can be isomerized under acidic conditions, for example, in the presence of hydrogen chloride at 20° to 120° C., to obtain the corresponding cis compound of formula Ib. In some instances, base-catalyzed trans to cis isomerizations can occur. For example, treatment of the compund of formula Ia in which $R^1$ is 7-bromo, $R^2$ is methyl, and $R^3$ and $R^4$ are ethyl with a solution of sodium methoxide in hexamethylphosphoramide at 150° to 200° C. for 10 to 30 hours afforded the corresponding cis compound of formula Ib in which $R^1$ is 7-bromo, $R^2$ is methyl, and $R^3$ and $R^4$ are ethyl.

The following examples illustrate further this invention.

EXAMPLE 1

3-(2-Hydroxyethyl)-1,4-dimethyl-2-piperazinone (V; $R^5$=Me)

The mixture of sym. dimethylethylenediamine (1 eq, 53 g), bromobutyrolactone (1 eq, 100 g) and triethylamine (1 eq, 120 ml) in 1000 mL of tetrahydrofuran was refluxed overnight. The crude precipitate was filtered and thoroughly washed with diethyl ether. The ether was evaporated and the residue was purified by elution through a silica gel column using 2% (v/v) methanol in chloroform to obtain the title compound. A small sample was converted into a picrate and crystallized from methanol to obtain the picrate salt of the title compound: mp 157°–159° C.; IR (KBr) 3220, 1650, 1565 and 1330 cm$^{-1}$; UV max (MeOH) 353 nm ($\epsilon$ 18090); and NMR (DMSO-d$_6$) $\delta$ 2.1 (m, 2H), 2.9 and 2.93 (singlets, 6H), 3.5 (m, 6H), 3.95 (m, 1H), and 8.55 (s, 2H).

In the same manner but replacing sym. dimethylethylenediamine with an equivalent amount of sym. diethylethylenediamine, the following compound of formula V was obtained, 1,4-diethyl-3-(2-hydroxyethyl)-2-piperazinone picrate: mp 127°–129° C. (crystallized from methanol-diethyl ether); IR (mineral oil) 3290, 1640, 1565 and 1315 cm$^{-1}$; UV max (MeOH) 354 nm ($\epsilon$ 15675); and NMR (DMSO-d$_6$) $\delta$ 1.05 and 1.25 (triplets, J=7.5 Hz, 6H), 2.04 (q, J=5.5 Hz, 2H), 3.05–3.75 (m, 10H), 3.95 (t, J=5.5 Hz, 1H), and 8.55 (s, 2H).

EXAMPLE 2

3-(2-Chloroethyl)-1,4-dimethyl-2-piperazinone (VI: $R^5$=Me and X=Cl)

Thionyl chloride (1.5 mL) was added dropwise to an ice cooled methylene chloride (5 mL) solution of 3-(2-hydroxyethyl)-1,4-dimethyl-2-piperazinone (0.40 g, described in Example 1). The reaction mixture was stirred for 30 min and poured on an ice solution of 10% sodium bicarbonate. The mixture was extracted with methylene chloride, and the organic extract was dried and evaporated to give the title compound: IR (CHCl$_3$) 1635 cm$^{-1}$; and NMR (CDCl$_3$) $\delta$ 2.35 (s, 3H) and 2.90 (s, 3H).

In the same manner, but replacing 3-(2-hydroxyethyl)-1,4-dimethyl-2-piperazinone with an equivalent amount of 1,4-diethyl-3-(2-hydroxyethyl)-2-piperazinone (described in Example 1), the following compund of formula VI was obtained, 3-(2-chloroethyl)-1,4-diethyl-2-piperazinone; IR (CHCl$_3$) 1635 cm$^{-1}$; and NMR (CDCl$_3$) $\delta$ 1.1 (t, 6H) and 3.65 (t, 2H).

EXAMPLE 3

1,4-Dimethyl-3-[2-(2,3-dihydro-3-methyl-1H-indol-1-yl)ethyl]-2-piperazinone (VIII: $R^1$=H, and $R^2$ and $R^5$=Me)

2,3-Dihydro-3-methylindole (3.99 g, 1 eq, described by A. Smith and J. H. P. Utley, Chem. Commun., 1965, 427) and 3-(2-chloroethyl)-1,4-dimethyl-2-piperazinone (5.7 g, 1 eq, described in Example 2) were combined in toluene (100 mL) and refluxed overnight. The cold mixture was poured into an ice solution of 10% sodium bicarbonate and the product was extracted with methylene chloride. Evaporation of the extract gave 9 g of crude product. The crude product was passed through a silica gel column using 3% (v/v) methanol in chloroform to give the title compound (6 g): IR (CHCl$_3$) 1640 cm$^{-1}$; UV max (MeOH) 296 nm ($\epsilon$ 2300) and 257 (5900); and NMR (CDCl$_3$) $\delta$ 1.25 (d, 3H), 2.35 (s, 3H), 2.8 (s, 3H) and 6.35–7.1 (m, 4H).

In the same manner, but replacing 3-(2-chloroethyl)-1,4-dimethyl-2-piperazinone with an equivalent amount of 3-(2-chloroethyl)-1,4-diethyl-2-piperazinone (described in Example 2), the following compound of formula VIII was obtained, 1,4-diethyl-3-[2-(2,3-dihydro-3-methyl-1H-indol-1-yl)ethyl]-2-piperazinone; IR (CHCl$_3$) 1635 cm$^{-1}$; UV max (MeOH) 298 nm ($\epsilon$ 2800) and 251 (9500); and NMR (CDCl$_3$) $\delta$ 1.1 (m, 6H), 1.25 (d, 3H) and 6.4–7.15 (m, 4H).

EXAMPLE 4

1,4-Dimethyl-3-[2-(3-methyl-1H-indol-1-yl)ethyl]-2-piperazinone (II: $R^1$=H, $R^2$ and $R^5$=Me)

A suspension of 1,4-dimethyl-3-[2-(2,3-dihydro-3-methyl-1H-indol-1-yl)ethyl]-2-piperazinone (3.5 g, described in Example 3), manganese dioxide (3.5 g) and 5% palladium on charcoal (0.35 g) in xylene (200 mL) was refluxed overnight. The hot suspension was filtered and the filtrate was evaporated to dryness giving 3 g of the title compound. The title compound was converted into the maleate salt and crystallized from methanol-diethyl ether: mp 130°–134° C.; IR (mineral oil) 2370, 1950 and 1665 cm$^{-1}$; UV max (MeOH) 290 nm ($\epsilon$ 5625) and 225 (36100); NMR (DMSO-d$_6$) $\delta$ 2.2 (s, 3H), 2.5 (s, 3H), 2.8 (s, 3H), 6.15 (s, 2H) and 7.2 (m, 4H); and Anal. Calcd for $C_{17}H_{23}N_3O \cdot C_4H_4O_4$: C, 62.83% H, 6.78% N, 10.47% and Found: C, 62.41% H, 6.75%, N, 10.29%.

In the same manner, but replacing 1,4-dimethyl-3-[2-(2,3-dihydro-3-methyl-1H-indol-1-yl)ethyl]-2-piperazinone with an equivalent amount of 1,4-diethyl-3-[2-(2,3-dihydro-3-methyl-1H-indol-1-yl)ethyl]-2-piperazinone (described in Example 3), the following compound of formula II was obtained, 1,4-diethyl-3-[2-(3-methyl-1H-indol-1-yl)ethyl]-2-piperazinone: IR (CHCl$_3$) 1640 cm$^{-1}$; UV max (MeOH) 290 nm ($\epsilon$ 5800), 258 (5400), 251 (5500) and 226 (26400); and NMR (CDCl$_3$) $\delta$ 1.1 (m, 6H), 2.3 (s, 3H), 4.15 (m, 2H), 6.88 (s, 1H), and 7.05–7.6 (m, 4H).

EXAMPLE 5

(4a,12a-cis)-1,4,5-Trimethyl-1,2,3,4,4a,11,12,12a-octahydropyrazino[2',3'-3,4]-pyrido[1,2-a]indol (Ib: $R^1$=H, and $R^2$, $R^3$ and $R^4$=Me)

A solution of 1,4-dimethyl-3-[2-(3-methyl-1H-indol-1-yl)ethyl]-2-piperazinone (2.5 g, described in Example 4) in phosphorous oxychloride (10 mL) was refluxed for 3.5 hr. Benzene (50 mL) was added to the mixture and the mixture was evaporated under vacuum. The residue was dissolved in absolute ethanol and 1.5 g of sodium metal was added in small portions under nitrogen. Water was added to the sodium free ethanolic solution and the solution was extracted with diethyl ether. Evaporation of the extract gave 2.5 g of crude product. Chromatography on silica gel using 5% (v/v) methanol in chloroform yielded 0.7 g of the title compound. The title compound was converted to the dihydrochloride salt of the title compound and crystallized from acetonitrile: mp 210°–212° C.; IR (mineral oil) 2430; UV max (MeOH) 282 nm ($\epsilon$ 6710), 276 (7210) and 225 (31790); NMR (DMSO-d$_6$) $\delta$ 2.35 (s, 3H), 2.65 (s, 3H), 3.0 (s, 3H), 5.2 (br, s, 1H), 7.3 (m, 4H) and 7.93 (s, 1H); and Anal. Calcd for $C_{15}H_{23}N_3 \cdot HCl$: C, 59.29% H, 7.90% N, 12.20% and Found: C, 59.39% H, 8.07% N, 12.14%.

In the same manner, but replacing 1,4-dimethyl-3-[2-(3-methyl-1H-indol-1-yl)ethyl]-2-piperazinone with an equivalent amount of 1,4-diethyl-3-[2-(3-methyl-1H-indol-1-yl)ethyl]-2-piperazinone (described in Example 4), the following compound of formula Ib was obtained, (4a,12a-cis)-1,4-diethyl-5-pyrido[1,2-a]indole as the dihydrochloride salt; mp 283°–240° C. (crystallized from methanol-diethyl ether); IR (mineral oil) 2350 cm$^{-1}$; UV max (MeOH) 284 nm ($\epsilon$ 7900), 277 (8325) and 228 (38430); NMR (DMSO-d$_6$) $\delta$ 1.25 (m, 6H), 2.35 (s, 3H), 5.25 (br s, 1H) and 7.3 (m, 4H); and Anal. Calcd for $C_{19}H_{27}N_3 \cdot 2HCl$: C, 61.61% H, 7.89% N, 11.35% and Found: C, 60.89% H, 8.19% N, 10.92%.

EXAMPLE 6

3-Methyl-1H-indole-1-butanoic Acid (X: $R^1$=H and $R^2$=Me)

3-Methylindole (13.1 g; 1 eq) and sodium hydride (5 g of 50% suspension—1 eq) were melted together in a 3-neck round bottom flask immersed in 100° C. oil bath until evolution of hydrogen gas ceased. The mixture was cooled down and dissolved in 250 mL of dry dimethylformamide. Butyrolactone (17.2 g—2 eq) was added and the solution was refluxed for 7 hr and poured on ice. The mixture was extracted with diethyl ether, and the acid was liberated with 10% hydrochloric acid solution. The mixture was extracted with diethyl ether. Evaporation of the extract gave a residue which was chromatographed on silica gel using 10% (v/v) ethyl acetate in benzene. Evaporation of the appropriate eluates gave 5.5 g of the title compound, mp 82°–84° C.

EXAMPLE 7

10-Methyl-6,7,8,9-tetrahydropyrido[1,2-a]indol-9-one (XI: $R^1$=H and $R^2$=Me)

3-Methyl-1H-indole-1-butanoic acid (5 g, described in Example 6) was suspended in polyphosphoric acid and the mixture was heated at 100° C. for 1 hr, cooled, and poured on ice. The mixture was extracted with diethyl ether. The extract was washed with 10% aqueous sodium bicarbonate, evaporated (4.4 g of crude product) and chromatographed through silica gel using 5% methanol in chloroform (v/v).

The appropriate eluates were evaporated to give the title compound: mp 87°–89° C.; IR (CHCl$_3$) 1648 cm$^{-1}$; UV max (MeOH) 316 nm ($\epsilon$ 21611) and 241 (26009); NMR (CDCl$_3$) $\delta$ 2.2 (m, 2H), 2.5 (m, 2H), 2.58 (s, 3H), 4.0 (t, 2H), 7.1 (m, 3H) and 7.4 (m, 1H); and Anal. Calcd for $C_{13}H_{13}NO$: C, 78.36% H, 6.58% N, 7.03% and Found: C, 78.16% H, 6.84% N, 7.07%.

EXAMPLE 8

2-Bromo-10-methyl-6,7,8,9-tetrahydropyrido[1,2-a]indol-9-one (XI: $R^1$=2-Br and $R^2$=Me)

Aged N-bromosuccinimide (1 g) was added in small portions to a solution of 10-methyl-6,7,8,9-tetrahydropyrido[1,2-a]indol-9-one (described in Example 7, 1.0 g), in methylene chloride (50 mL). The mixture was stirred at room temperature for 30 min, washed successively with water, 5% aqueous sodium bicarbonate, and water again. After drying (MgSO$_4$ and filtration), the solvent was evaporated, and the residue was crystallized from diethyl ether, mp 142°–144° C.; yield 1.25 g; NMR (CDCl$_3$) $\delta$ 2.34 (m, 2H), 2.57 (s, 3H), 2.68 (m, 2H), 4.11 (t, J=5.5 Hz, 2H), 7.10 (d, $J_{34}$=8.5 Hz, 1H), 7.37 (dd, $J_{34}$=8.5 Hz, $J_{13}$=2 Hz, 1H) and 7.75 (d, $J_{13}$=2 Hz, 1H).

EXAMPLE 9

8-Bromo-10-methyl-6,7,8,9-tetrahydropyrido[1,2-a]indol-9-one (IV: $R^1$=H, $R^2$=Me and X=Br)

The reaction was performed in the dark (the flask wrapped in a tin-foil), and with the provision for maintaining a nitrogen atmosphere. To a solution of 10-methyl-6,7,8,9-tetrahydropyrido[1,2-a]indol-9-one (described in Example 7, 49.75 g) in methylene chloride (250 mL) was added a solution of trimethylphenylammonium tribromide (94 g) in methylene chloride (1200 mL) as fast as possible (over 2 min); the inside temperature was maintained at 10° C. The reaction mixture was stirred at room temperature for 30 hr, evaporated in vacuo, and the solid residue was partitioned between water (600 mL) and benzene-diethyl ether 1:1 (800 mL, v/v). The separated organic layer was dried (MgSO$_4$), filtered, and the filtrate was evaporated. The crude product was dissolved in chloroform (55 mL), and diethyl ether (600 mL) was added at once, whereby a voluminous, dark-green material precipitated. It was quickly removed by filtration (without suction), and the filtrate was chilled to 0° C. The crystals which formed were collected by filtration; 38 g, mp 126°–128° C. This material was recrystallized from chloroform-diethyl ether (1:8, v/v) to give 35 g of the title compound, mp 131°–133° C.; IR (CHCl$_3$) 1665–1660, and 1535 cm$^{-1}$; UV max (MeOH) 246 and 327 nm, ($\epsilon$ 16000) and (18200) respectively; NMR (CDCl$_3$) δ 2.67 (br s, 3H), overlapping with 2.65 (m, 2H), 4.29 (dd, $J_1$=7.5 Hz, $J_2$=4.5 Hz, 2H), 4.67 (t, J=4 Hz, 1H), 7.25–7.7 (m, 4H); Anal. Calcd for C$_{13}$H$_{12}$BrNO: C, 56.12% H, 4.35% N, 5.03% and Found: C, 56.20% H, 4.32% N, 5.05%.

EXAMPLE 10

2,8-Dibromo-10-methyl-6,7,8,9-tetrahydropyrido[1,2-a]indol-9-one (IV: R$^1$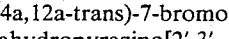 2-Br, R$^2$=Me and X=Br).

Aged N-bromosuccinimide (4.89 g, 27.5 mmol) was added in small portions (over 15 min) to a solution of 2-bromo-10-methyl-6,7,8,9-tetrahydropyrido[1,2-a]indol-9-one (described in Example 8, 5.0 g) in methylene chloride (100 mL) and stirring at room temperature was continued for 30 min. This crude mixture was then protected against light, and a solution of bromine (2 mL) in methylene chloride (200 mL) was added very slowly from a dropping funnel. The reaction mixture was washed successively with cold water, 5% sodium bicarbonate, and water again. After drying (MgSO$_4$) and filtration, the solvent was evaporated, and the title compound was crystallized from chloroform, mp 156° C.; yield 6.6 g; Anal. Calcd for C$_{13}$H$_{11}$Br$_2$NO: C, 43.72% H, 3.10% N, 3.92% and Found: C, 43.35% H, 3.00% N, 3.99%.

EXAMPLE II (4a,12a-trans)-5-Methyl-1,2,3,4,4a,11,12,12a-octahydropyrazino[2',3'-3,4]-pyrido[1,2-a]indole (I: R$^1$, R$^3$ and R$^4$=H and R$^2$=Me)

A solution of ethylenediamine (11 mL, 9.9 g, 165 mmol) in dioxane (11 mL) was added at once to a solution of 8-bromo-10-methyl-6,7,8,9-tetrahydropyrido[1,2-a]indol-9-one (described in Example 9, 8.34 g, 30 mmol) in the same solvent (75 mL) while the inside temperature was maintained at 15° C. and nitrogen was being introduced in the reaction apparatus. The mixture was stirred at room temperature for 18 hr, cooled in an ice-water bath, and diluted with methanol (75 mL). Water (1 mL) was added, and upon cooling and stirring, sodium borohydride (3.1 g, 82 mmol, pulverized) was slowly added in portions. After the borohydride addition was complete, stirring was continued for 2 hr, the mixture was poured (upon cooling) into 10% hydrochloric acid (90 mL), and the pH of the resultant solution was adjusted to 2. The solution was washed with diethyl ether (150 mL), and the aqueous solution was basified (pH 10–11) with 50% sodium hydroxide upon strong cooling. The product was extracted with benzene-diethyl ether (2:1 v/v, 2×350 mL). The combined extracts were dried (MgSO$_4$), filtered, and evaporated to give 5.5 g of the title compound (mp 190°–192° C.). The title compound was crystallized from hot acetonitrile: mp 196°–197° C.; IR (CHCl$_3$) 3340 and 3290 cm$^{-1}$; NMR (CDCl$_3$) δ 1.67 (s, 2H), 1.90 (m, 2H), 2.44 (s, 3H), 2.98 (m, 4H), 2.5–2.9 and 3.15–4.4 (m), 7.10 (m, 3H) and 7.42 (m, 1H); Anal. Calcd for C$_{15}$H$_{19}$N$_3$: C, 74.65% H, 7.94% N, 17.41% and Found: C, 74.37% H, 7.85% N, 17.22%.

A methanolic solution of the title compound (1.7 g) was treated with a methanolic solution of maleic acid (1.4 g); isopropanol was added until the mixture became opalescent. On standing at room temperature for 18 hr, the salt crystallized. The salt was recrystallized from methanoldiethyl ether to give the maleate salt of the title compound; mp 229°–231° C.; Anal. Calcd for C$_{15}$H$_{19}$N$_3$·C$_4$H$_4$O: C, 63.85% H, 6.48% N, 11.76% and Found: C, 63.50% H, 6.41% N, 11.69%.

In the same manner but replacing 8-bromo-10-methyl-6,7,8,9-tetrahydropyrido[1,2-a]indol-9-one with an equivalent amount of 2,8-dibromo-10-methyl-6,7,8,9-tetrahydropyrido[1,2-a]indol-9-one (described in Example 10), the following compound of formula Ia was obtained; (4a,12a-trans)-7-bromo-5-methyl-1,2,3,4,4a,11,12,12a-octahydropyrazino[2',3'-3,4]pyrido[1,2-a]indole; mp 185° C. (crystallized from acetonitrile-methanol); NMR (CDCl$_3$) δ 1.66 (br s, 2H), 2.35 (s, 3H), 6.95 1 (d, $J_{89}$=8 Hz, 1H), 7.14 (dd, $J_{89}$=8 Hz, $J_{68}$=1 Hz, 1H) and 7.54 (br s, 1H); Anal. Calcd for C$_{15}$H$_{18}$BrN$_3$: C, 56.25% H, 5.66% N, 13.12% and Found: C, 56.04% H, 5.60% N, 13.07%.

The latter compound was dissolved in methanol and a solution of hydrogen chloride in diethyl ether was added. The precipitate was recrystallized from acetonitrile to obtain the hydrochloride salt of the latter compound: mp 282° C.; IR (mineral oil) 3350 and 2700 cm$^{-1}$; UV max (MeOH) 233, 286, and 293, ($\epsilon$ 37700), (6960) and (6960) resp.; NMR (DMSO-d$_6$) δ 2.42 (s, 3H), 4.34 (d, J=11 Hz, 1H), 7.25 (br s, 2H), and 7.67 (s, 1H); Anal. Calcd for C$_{15}$H$_{18}$BrN$_3$·HCl: C, 45.82% H, 5.13% N, 10.69% and Found: C, 45.59% H, 4.99% N, 10.87%.

EXAMPLE 12

(4a,12a-trans)-1,4-Diethyl-5-methyl-1,2,3,4,4a,11,12,-12a-octahydropyrazino-[2',3'-3,4]-pyrido[1,2-a]indole (Ia: R$^1$=H, R$^2$=Me and R$^3$ and R$^4$=Et)

A mixture of (4a,12a-trans)-5-methyl-1,2,3,4,4a,11,12,12a-octahydropyrazino[2',3'-3,4]pyrido[1,2-a]indole (described in Example 11), dimethylformamide (DMF, 225 mL), ethyl iodide (10 g, 64 mmol), and K$_2$CO$_3$ (8.83 g, 64 mmol) was stirred at room temperature overnight, then heated at 70° C. for 4 hr, cooled, and poured into 200 mL of water. Crude product was extracted with diethyl ether (3×150 mL), and the combined extracts were washed with water, dried (MgSO$_4$), filtered, and evaporated. The residue was applied on a column of silica gel; and elution with methylene chloride-methanol (20:1, v/v) afforded 3.5 g of the title compound: NMR (CDCl$_3$) δ 1.04 and 1.10 (J=7.5 Hz, 6H), 1.3–2.1 (m, 2H), 2.43 (s, 3H), 2.55 (m, 4H), 3.15 (overlapping quartets, J=7.5 Hz, 4H), 3.55–4.4 (m, 4H), 7.1 (m, 3H), 7.45 (m, 1H).

The title compound (6 g) was dissolved in methanol (80 mL) and a methanolic solution of hydrogen bromide (0.0574 g of HBr/mL, 30 mL=1.6 g) was added. The hydrobromide salt of the title compound crystallized out, it was collected by filtration and recrystallized from methanol-acetonitrile 15:85 (v/v) yield 5.76 g; mp 237°–238° C.; IR (mineral oil) 2600 cm$^{-1}$; UV max (MeOH) 229 and 286 nm, ($\epsilon$ 38510) and (8020) resp.; NMR (DMSO-d$_6$) $\delta$ 1.03 and 1.29 (t, J=7.5 Hz, 6H), 2.32 (s, 3H), 4.74 (d, J=11 Hz, 1H); and Anal. Calcd for C$_{19}$H$_{27}$N$_3$.HBr: C, 60.31%, H, 7.46% N, 11.10% and Found: C, 60.41% H, 7.50% N, 11.45%.

In the same manner but replacing ethyl iodide with an equivalent amount of propyl iodide the following compound of formula I was obtained, (4a,12a-trans)-5-methyl-1,4-dipropyl-1,2,3,4,4a,11,12,12a-octahydropyrazino[2',3'-3,4]pyrido[1,2-a]indole: NMR (CDCl$_3$) $\delta$ 0.81 and 0.93 (t, J=7.5 Hz, 6H), multiplets centered at 1.54 (4H), 2.42 (s, 3H); and the corresponding hydrobromide salt (crystallized from methanol): mp 246°–248° C.; IR (mineral oil) 2550 cm$^{-1}$; UV max (MeOH) 285 nm ($\epsilon$ 8070); NMR (DMSO-d$_6$) $\delta$ 0.80 and 0.97 (t, J=7 Hz), 4.76 (d, J=10 Hz, 1H), 6.75–7.55 (m, 4H); and Anal. Calcd for C$_{21}$H$_{31}$N$_3$.HBr: C, 62.06% H, 7.93% H, 10.34% and Found: C, 62.11% H, 8.11% N, 10.33%.

Similarly, use of ethyl bromoacetate gave (4a,12a-trans)-5-methyl-1,2,3,4,4a,11,12,12a-octahydropyrazino[2',3'-3,4]pyrido[1,2-a]indole-1,4-diacetic acid diethyl ester; NMR (CDCl$_3$) $\delta$ 1.20 and 1.27 (two triplets, J=7.5 Hz, 6H), 2.35 (s, 3H), 3.47 (br s, 4H); and the corresponding hydrochloride salt (crystallized from methylene chloride-diethyl ether): mp 183°–184° C.; IR (mineral oil) 2400, 1745, and 1740 cm$^{-1}$; UV max (MeOH) 229 and 286 nm ($\epsilon$=7470) and (7890) resp.; (DMSO-d$_6$) $\delta$ 1.15 and 1.28 (t, J=7.5 Hz, 6H), 2.05 (s, 3H), 2.27 (br s, 4H), 4.06 and 4.23 (quartets, J=7.5 Hz, 4H), 5.00 (d, J=10 Hz, 1H); and Anal. Calcd for C$_{23}$H$_{31}$N$_3$O$_4$.HCl: C, 61.38% H, 7.17% N, 9.34% and Found: C, 60.96% H, 7.16% N, 9.30%.

Similarly, condensation of ethyl iodide with (4a,12a-trans)-7-bromo-5-methyl-1,2,3,4,4a,11,12,12a-octahydropyrazino[2',3'-3,4]pyrido[1,2-a]indole gave (4a,12a-trans)-7-bromo-1,4-diethyl-5-methyl-1,2,3,4,4a,11,12,-12a-octahydropyrazino[2',3'-3,4]pyrido[1,2-a]indole: mp 130° C. (crystallized from diethyl ether); and NMR (CDCl$_3$) $\delta$ 1.02 and 1.07 (overlapping triplets, 6H), 2.35 (br s, 3H), 6.96 (d, J$_{89}$=8.5 Hz, 1H), 7.14 (dd, J$_{89}$=8.5 Hz, J$_{68}$=1 Hz, 1H), 7.55 (d, J$_{68}$=1 Hz, 1H); and the corresponding hydrochloride salt (crystallized from acetonitrile): mp 290°–291° C.; IR (mineral oil) 3400, and 2400 cm$^{-1}$; UV max (MeOH) 233, 288, and 294 nm ($\epsilon$=35550), (6650) and (6900) resp.; NMR (DMSO-d$_6$) $\delta$ 1.02 and 1.29 (t, J=7.5 Hz, 6H), 2.31 (s, 3H), 4.96 (d, J=10 Hz, 1H), 7.20 (m, 2H), 7.57 (d, J=Hz, 1H), 11.5 (br, exchangeable, 1H); and Anal. Calcd for C$_{19}$H$_{26}$BrN$_3$.HCl: C, 55.27% H, 6.59% N, 10.18% and Found: C, 55.39% H, 6.52% N, 10.26%.

EXAMPLE 13

(4a,12a-trans)-1-Ethyl-5-methyl-1,2,3,4,4a,11,12,12a-octahydropyrazino[2',3'-3,4]pyrido[1,2-a]indole (Ia: R$^1$ and R$^3$=H, R$^2$=Me and R$^4$=Et)

To a solution of (4a,12a-trans)-5-methyl-1,2,3,4,4a-11,12,12a-octahydropyrazino[2',3'-3,4]pyrido[1,2-a]indole (4.82 g, 20 mmol, described in Example 11) in DMF (200 mL) was added anhydrous K$_2$CO$_3$ (3.45 g, 25 mmol), and ethyl iodide (3.9 g, 25 mmol). The mixture was stirred at room temperature for 3 hr, and evaporated. The residue was partitioned between water and chloroform, and the organic phase was separated, dried (MgSO$_4$), filtered and evaporated. The residue was chromatographed on silica gel (200 g) using chloroform-methanol (99:1, v/v) to give 3.6 g of the title compound: NMR (CDCl$_3$) $\delta$ 1.06 (t, J=7.5 Hz, 3H), 1.83 (br s, 1H), 2.42 (s, 3H), 4.25 (dd, 1H).

The title compound was reacted with hydrogen bromide to obtain the dihydrobromide salt of the title compound: mp 237°–238° C. (crystallized from methanol-diethyl ether); UV max (MeOH) 285 nm ($\epsilon$ 7,400), 277 (7,700), 236 (34,700); and Anal. Calcd for C$_{17}$H$_{23}$N$_3$.2HBr: C, 47.34% H, 5.84% N, 9.74% and Found: C, 47.13% H, 6.01% N, 9.82%.

In the same manner, but replacing ethyl iodide with an equivalent amount of 2-iodopropane, the following compound of formula Ia was obtained, (4a,12a-trans)-5-methyl-1-(1-methylethyl)-1,2,3,4,4,a,11,12,12a-octahydropyrazino[2',3'-3,4]pyrido[1,2-a]indole: mp 125°–126° C. (crystallized from acetonitrile); NMR (CDCl$_3$) $\delta$ 0.92 and 1.17 (doublets, 6H), 2.46(br s, 3H), 1.80 (s, 1H); and the dihydrochloride salt thereof: mp 239°–241° C. (crystallized from methanol); IR (mineral oil) 3500, 3420 and 2500 cm$^{-1}$; UV max (MeOH) 285, 278, and 226 nm ($\epsilon$ 7660), (7550), and (37200) resp.; NMR (DMSO-d$_6$) $\delta$ 1.20 and 1.41 (doublets, J=7 Hz, 6H), 2.47 (br s, 3H), 5.33 (d, J=10 Hz, 1H), 6.9-7.6 (m, 4H); and Anal. Calcd for C$_{18}$H$_{25}$N$_3$.2HCl: C, 60.67% H, 7.63% N, 11.78% and Found: C, 59.40% H, 7.55%, N, 11.49%.

Similarly, replacement of ethyl iodide by 3-bromopropyne gave (4a,12a-trans)-5-methyl-1-(2-propynyl)-1,2,3,4,4a,11,12,12a-octahydropyrazino[2',3'-3,4]pyrido[1,2-a]indole: NMR (CDCl$_3$) $\delta$ 2.51 (s, 3H), 2.84 and 2.91 (doublets, 1H+2H); and the dihydrochloride salt thereof: mp 220°–221° C. (crystallized from methanol-diethyl ether); IR (mineral oil) 3300, 3200, 2660, 2320, and 2120 cm$^{-1}$; UV max (MeOH) 227, 277, and 285 nm ($\epsilon$ 34600), (7160) and (7020) resp.; NMR (DMSO-d$_6$) $\delta$ 2.47 (s, 3H), 4.88 (d, J=11 Hz, 1H), 5.45 (br, 3H), 6.95-7.6 (m, 4H); Anal. Calcd for C$_{18}$H$_{21}$N$_3$.2HCl; C, 61.36% H, 6.58% N, 11.93% and Found: C, 60.87% H, 6.82% N, 11.86%.

Similarly, replacement of ethyl iodide by 2-(phenoxy)ethyl bromide gave (4a,12a-trans)-5-methyl-1-[2-(phenoxy)ethyl]-1,2,3,4,4a,11,12,12a-octahydropyrazo[2',3'-3,4]pyrido[1,2-a]indole: NMR (CDCl$_3$) $\delta$1.72 (s, 1H), 2.41 (s, 3H), 4.00 (m, 5H), 6.65-7.60 (m, 9H); and the maleate salt thereof: mp 177°–178° C. (crystallized from methanol-diethyl ether); IR (mineral oil) 3300, 2500, 1700, and 1585 cm$^{-1}$; UV max (MeOH) 224, 272, and 276 nm ($\epsilon$ 50190), (9030), and (9500) resp.; NMR (DMSO-d$_6$) $\delta$ 2.38 (s, 3H), 5.97 (s, 2H), 6.75-7.55 (m, 9H); and Anal. Calcd for C$_{23}$H$_{27}$N$_3$O.C$_4$H$_4$O$_4$: C, 67.90% H, 6.54% N, 8.80% and Found: C, 57.59% H, 6.50% N, 8.70%.

Similarly, replacement of ethyl iodide by ethyl bromoacetate gave (4a,12a-trans)-5-methyl-1,2,3,4,4a,11,12,-12a-octahydropyrazino[2',3'-3,4]pyrido[1,2-a]indole-1-acetic acid ethyl ester: NMR (CDCl$_3$) $\delta$ 1.26 (t, 3H), 2.47 (s, 3H), 3.47 (s, 2H), 4.19 (q, 2H), 7.12 (m, 3H) and 7.48 (m, 1H); and the maleate salt thereof: mp 203°–204° C. (crystallized from ethanol); and Anal. Calcd for C$_{19}$H$_{25}$N$_3$O$_2$.C$_4$H$_4$O$_4$: C, 62.29% H, 6.59% N, 9.48% and Found: C, 61.97% H, 6.66% N, 9.34%.

Similarly, reaction of 2-iodopropane with (4a,12a-trans)-7-bromo-5-methyl-1,2,3,4,4a,11,12,12a-octahydropyrazino[2',3'-3,4]pyrido[1,2-a]indole gave (4a,12a-trans)-7-bromo-5-methyl-1-(1-methylethyl)-1,2,3,4,4a,11,12,12a-octahydropyrazino[2',3'-3,4]pyrido[1,2-a]indole: mp 138° C. (crystallized from diethyl ether); NMR (CDCl$_3$) δ 0.93 and 1.18 (doublets, J=7 Hz, 6H), and 7.59 (d, 1H); and Anal. Calcd for C$_{18}$H$_{24}$BrN$_3$: C, 59.66% H, 6.68% N, 11.60% and Found: C, 59.49% H, 6.64% N, 11.58%.

EXAMPLE 14

(4a,12a-trans)-1,4,5-Trimethyl-1,2,3,4,4a,11,12,12a-octahydropyrazino[2',3'-3,4]pyrido[1,2-a]indole (Ia: R$^1$=H, and R$^2$, R$^3$ and R$^4$=Me)

To a solution of (4a,12a-trans)-5-methyl-1,2,3,4,4a,11,12,12a-octahydropyrazino[2',3'-3,4]pyrido[1,2-a]indole (5.5 g, described in Example 11) in methanol (150 mL) was added a diethyl ether solution saturated with HCl (20 mL), and the mixture was evaporated. The residue was dissolved in 37% aqueous formaldehyde and stirred at room temperature for 2 hr. Upon cooling, the reaction mixture was treated dropwise with a solution of sodium cyanoborohydride (7.6 g) in methanol (400 mL). Molecular sieves (16.5 g) were added, and stirring was continued overnight. After filtration, methanol was evaporated, and the residue was partitioned between 5% ammonium hydroxide and chloroform. The organic layer was separated, evaporated, and the oily product (6.1 g) was chromatographed on silica gel. Elution with AcOEt-hexane-Et$_3$N (60:35:5, v/v) afforded the title compound (4.2 g) as an oil: NMR (CDCl$_3$) δ 2.32 (s, 3H), 2.38 (s, 3H), and 2.42 (s, 3H).

The corresponding monomaleate salt of the title compound was crystallized from methanol: mp 178°-180° C.; IR (CHCl$_3$) 2400, 1900, 1700, 1570, and 1345 cm$^{-1}$; UV max (MeOH) 226, 279, and 285 nm (ε 42710), (7790), and (8170) resp.; NMR (CDCl$_3$) δ 2.35 (br s, 6H), 2.89 (s, 3H), 2.05-4.45 (m, 9H), 4.70 (d, J=10 Hz, 1H), 6.22 (s, 3H), 7.12 (m, 3H), 7.49 (m, 1H); and Anal. Calcd for C$_{17}$H$_{23}$N$_3$.C$_4$H$_4$O$_4$: C, 65.43% H, 7.06% N, 10.90% and Found: C, 65.59% H, 6.99% N, 10.82%.

EXAMPLE 15

(4a,12a-trans)-5-Methyl-1,2,3,4,4a,11,12,12a-octahydropyrazino[2',3'-3,4]pyrido[1,2-a]indole-1,4-diethanol (Ia: R$^1$=H, R$^2$=Me, and R$^3$ and R$^4$=CH$_2$CH$_2$OH)

(4a,12a-trans)-5-Methyl-1,2,3,4,4a,11,12,12a-octahydropyrazino[2',3'-3,4]-pyrido[1,2-a]indole-1,4-diacetic acid diethyl ester (2.07 g, described in Example 12) was dissolved in anhydrous diethyl ether (50 mL); the solution was filtered and added dropwise to a stirred suspension of LiAlH$_4$ (0.835 g) in diethyl ether (30 mL) over 5 min. The reaction mixture was refluxed for 14 hr, cooled and decomposed (under nitrogen) by a successive addition of water (4.17 mL), 15% sodium hydroxide (4.17 mL), and water (4.17 mL) again. The resultant slurry was stirred for 60 min, filtered, and the filtrate was dried (MgSO$_4$) and evaporated. The filter cake was extracted with chloroform, the extracts were filtered, and combined with the material obtained from the ethereal phase. There was obtained 1.05 g (64%) of the title compound.

The corresponding dihydrochloride was prepared in a chloroform solution by addition of a solution of HCl in diethyl ether, and evaporation to dryness. The residual solids were crystallized from ethanol-diethyl ether and recrystallized from methanol-diethyl ether, mp 202° C.; IR (mineral oil) 3200 and 2600 cm$^{-1}$; UV max (MeOH) 227 and 286 nm (ε 39230) and (8010) resp.; NMR (DMSO-d$_6$) δ 2.38 (s, 3H), 5.16 (d, J=11 Hz, 1H), 5.13 and 5.25 (broad singlets, 4H), 6.9-7.6 (m, 4H); and Anal. Calcd for C$_{19}$H$_{27}$N$_3$O$_2$.2HCl: C, 56.71% H, 7.26% N, 10.44% and Found: C, 56.67% H, 7.51% N, 10.27%.

EXAMPLE 16

(4a,12a-trans)-4-Acetyl-1-ethyl-5-methyl-1,2,3,4,4a,11,12,12a-octahydropyrazino[2',3'-3,4]-pyrido[1,2-a]indole (Ia: R$^1$=H, R$^2$=Me, R$^3$=COCH$_3$, and R$^4$=Et)

(4a,12a-trans)-1-Ethyl-5-methyl-1,2,3,4,4a,11,12,12a-octahydropyrazino[2',3'-3,4]pyrido[1,2-a]indole (1.0 g, described in Example 13) in 60 ml of methylene chloride was added to 6 ml of 10% solution of sodium hydroxide, followed by dropwise addition of 0.8 ml of acetyl chloride. The mixture was stirred at room temperature for 1 hr, poured on ice and extracted with methylene chloride. Evaporation of the solvent gave 2.2 g of crude product. Chromatography on neutral alumina (chloroform) gave 1.15 g of the title compound. The basic product was converted to the hydrobromide salt and crystallized from methanol-diethyl ether: mp 230°-231° C.; IR (mineral oil) 2600, 1660 cm$^{-1}$; UV max (MeOH) 285 nm (ε 7750); 229 (37300); Anal. Calcd for C$_{19}$H$_{26}$BrN$_3$O: C, 58.16% H, 6.68% N, 10.71% and Found: C, 57.71% H, 6.70% N, 10.80% and NMR (DMSO-d$_6$) δ 1.29 (t, 3H), 2.10 (br s, 6H), 5.20 (m, 1H).

EXAMPLE 17

(4a,12a-trans)-1-Ethyl-5-methyl-4-propyl-1,2,3,4,4a,11,12,12a-octahydropyrazino[2',3'-3,4]pyrido[1,2-a]indole (Ia: R$^1$=H, R$^2$=Me, R$^3$=Pr and R$^4$=Et)

A mixture of (4a,12a-trans)-1-ethyl-5-methyl-1,2,3,4,4a,11,12,12a-octahydropyrazino[2',3'-3,4]pyrido[1,2-a]indole (7 g, 2.26 mmol, described in Example 13), DMF (200 mL), K$_2$CO$_3$ (14.4 g, 104 mmol), and 1-iodopropane (17.6 g, 10.4 mL, 104 mmol) was stirred at room temperature for 48 hr. After adding K$_2$CO$_3$ (4 g) and 1-iodopropane (5 ml), stirring was continued at 90° C. for 4 hr. The latter operation was repeated. The cold reaction mixture was poured into 200 mL of water, and extracted with diethyl ether (3X70 mL). The combined extracts were washed with water, dried (MgSO$_4$), filtered, and evaporated. The residual oil (4.5 g) was chromatographed on silica gel; elution with a mixture of hexane-AcOEt-Et$_3$N (6:3:1, v/v) afforded 3.8 g of the title compound: NMR (CDCl$_3$) δ 0.82 (t, J=7.5 Hz, 3H), 1.10 (t, J=7.5 Hz, 3H), 2.41 (s, 3H).

The title compound was dissolved in methanol and converted to the corresponding hydrobromide salt: mp 252°-254° C. (crystallized from methanol); IR (mineral oil) 2600 cm$^{-1}$; UV max (MeOH) 229 and 286 nm, (ε 39200) and (7960) resp.; NMR (DMSO-d$_6$) δ 0.8 (t, J=7.5 Hz, 3H), 1.29 (t, J=7.5 Hz, 3H), 2.32 (s, 3H), 4.79 (d, J=10 Hz, 1H); and Anal. Calcd for C$_{20}$H$_{29}$N$_3$.HBr: C, 61.22% H, 7.44% N, 10.70% and Found: C, 61.20% H, 7.74% N, 10.87%.

Similarly, but replacing 1-iodopropane with 1-iodobutane, the following compound of formula Ia was obtained, (4a,12a-trans)-4-butyl-1-1-ethyl-5-methyl-1,2,3,4,4a,11,12,12a-octahydropyrazino[2',3'-3,4]pyrido[1,2-a]indole and the corresponding dihydrochloride salt thereof; mp 221°-222° C. (crystallized from acetonitrile-diethyl ether; IR (mineral oil) 3300 and 2400 cm$^{-1}$; UV max (MeOH) 227 and 285 nm (ε 34980) and (6770) resp.; NMR (DMSO-d$_6$) δ 0.83 (t, J=6 Hz, 3H), 1.32 (t, J=7 Hz, 3H), 2.40 (s, 3H), 5.19 (d, J=10 Hz, 1H), 6.85–7.55 (m, 4H); and Anal. Calcd for $C_{21}H_{31}N_3 \cdot 2HCl$: C, 63.30% H, 8.35% N, 10.55% and Found: C, 62.64% H, 8.12% N, 10.43%.

Similarly, but replacing 1-iodopropane with ethyl bromoacetate, the following compound of formula Ia was obtained, (4a,12a-trans)-1-ethyl-5-methyl-1,2,3,4,4a,11,12,12a-octahydropyrazino[2′,3′-3,4]pyrido[1,2-a]indole-4-acetic acid ethyl ester: NMR (CDCl₃) δ 1.10 and 1.21 (t, J=7.5 Hz, 6H), 2.36 (s, 3H), 3.44 (s, 2H), and 4.12 (q, J=7.5 Hz, 2H), and the corresponding hydrochloride salt thereof: mp 260°–261° C. (crystallized from ethanol); IR (mineral oil) 2460, and 1735 cm⁻¹; UV max (MeOH) 229 and 286 nm (ε 33750) and (8075) resp.; NMR (DMSO-d₆) δ 1.15 and 129 (t, J=7 Hz, 6H), 2.26 L (s, 3H), 4.05 (q, J=7 Hz, 2H), 4.97 (d, J=11 Hz, 1H), 6.8–7.5 (m, 4H); and Anal. Calcd for $C_{21}H_{29}N_3O_2 \cdot HCl$: C, 64.35% H, 7.71% N, 10.72% and Found: C, 64.19% H, 7.69% N, 10.71%.

Similarly, condensation of ethyl bromide with (4a,12a-trans)-5-methyl-1-(1-methylethyl)-1,2,3,4,4a,11,12,12a-octahydropyrazino[2′,3′-3,4]pyrido[1,2-a]indole (described in Example 13) gave (4a,12a-trans)-4-ethyl-5-methyl-1-(1-methylethyl)-1,2,3,4,4a,11,12,12a-octahydropyrazino[2′,3′-3,4]pyrido[1,2-a]indole: NMR (CDCl₃) δ 0.96 and 1.22 (doublets, J=7 Hz), 1.04 (t, J=7.5 Hz) and 2.41 (s, 3H); and the dihydrobromide salt thereof: mp 229°–230° C. (crystallized from methanol); IR (mineral oil) 3540, 3450, 2600 cm⁻¹; UV max (MeOH) 285 nm (ε 7855); NMR (DMSO-d₆) δ 1.1 (t, J=7 Hz), 1.28 and 1.4 (doublets, J=7 Hz), 2.37 (s, 3H), 5.23 (d, J=10 Hz, 1H), 6.85–7.55 (m, 4H); and Anal. Calcd for $C_{20}H_{29}N_3 \cdot 2HBr$: C, 50.75% H, 6.60% N, 8.79% and Found: C, 50.57% H, 6.51% N, 8.86%.

Similarly, condensation of 1-iodopropane with (4a,12a-trans)-5-methyl-1-(1-methylethyl)-1,2,3,4,4a,11,12,12a-octahydropyrazino[2′,3′-3,4]pyrido[1,2-a]indole (described in Example 13) gave (4a,12a-trans)-5-methyl-1-(1-methylethyl)-4-propyl-1,2,3,4,4a,11,12,12a-octahydropyrazino[2′,3′-3,4]pyrido[1,2-a]indole: NMR (DCDl₃) δ 0.8 (t, 3H), 0.96 and 1.16 (doublets, 6H) and 2.4 (s, 3H); the hydrobromide salt thereof: mp 255°–256° C. (crystallized from methanol): IR (mineral oil) 2500 cm⁻¹; UV max (MeOH) 228 and 285 nm, (ε 3900) and (8040) resp.; NMR (DMSO-d₆) δ 0.77 (t, J=7.5 Hz, 3H), 1.24 and 1.35 (doublets, J=7 Hz, 6H), 2.30 (s, 3H), 4.92 (d, J=10 Hz, 1H), 6.8–7.45 (m, 4H); and Anal. Calcd for $C_{21}H_{31}N_3 \cdot HBr$: C, 62.05% H, 7.93% N, 10.34% and Found: C, 61.71% H, 7.81% N, 10.23%.

Similarly, condensation of ethyl iodide with (4a,12a-trans)-5-methyl1,2,3,4,4a,11,12,12a-octahydro-1-(2-phenoxyethyl)-pyrazino[2′,3′-3,4]pyrido[1,2-a]indole (described in Example 13) gave (4a,12a-trans)-4-ethyl-5-methyl1,2,3,4,4a,11,12,12a-octahydro-1-(2-phenoxyethyl)-pyrazino[2′,3′-3,4]pyrido[1,2-a]indole; and the dihydrochloride salt thereof: mp 230°–231° C. (crystallized from methanol-diethyl ether); IR (mineral oil) 2440 cm⁻¹; UV max (MeOH) 224, 276, and 285 nm (ε 41900), (8740), and (8320) resp.; NMR (DMSO-d₆) δ 1.13 (t, J=6.5 Hz, 3H), 2.41 (s, 3H), multiplets centered at 2.2, 2.8, 3.65, and 4.35 (15H), 5.3 (d, J=9 Hz, 1H), 6.7–7.55 (m, 9H); and Anal. Calcd for $C_{25}H_{31}N_3O \cdot 2HCl$: C, 64.92% H, 7.19% N, 9.06% and Found: C, 64.92% H, 7.13% N, 9.02%.

Similarly, condensation of ethyl bromide with (4a,12a-trans)-7-bromo-5-methyl-1-(1-methylethyl)-1,2,3,4,4a,11,12,12a-octahydropyrazino[2′,3′-3,4]pyrido[1,2-a]indole (described in Example 13) gave (4a,12a-trans)-7-bromo-4-ethyl-5-methyl-1-(1-methylethyl)-1,2,3,4,4a,11,12,12a-octahydropyrazino[2′,3′-3,4]pyrido[1,2-a]indole: mp 125° C. (crystallized from diethyl ether); NMR (CDCl₃) δ 0.95 and 1.16 (doublets, J=7 Hz, 6H), 1.03 (t, 3H), and 7.58 (d, 1H); and Anal. Calcd for $C_{30}H_{28}BrN_3$: C, 61.53% H, 7.23% N, 10.77% and Found: C, 61.47% H, 7.20% N, 10.77%; and the corresponding dihydrochloride salt thereof: mp 228° C. (crystallized from methanol-isopropanol).

EXAMPLE 18

(4a,12a-cis)-5-Methyl-1-[2-(phenoxy)ethyl]-1,2,3,4,4,a,11,12,12a-octahydropyrazino[2′,3′-3,4]pyrido[1,2-a]indole (Ib: R¹ and R³=H, R²=Me and R⁴=CH₂CH₂O—C₆H₅)

In the initial attemps to form the maleate and dimethansulfonate salts of (4a,12a-trans)-5-methyl-1-[2-(phenoxy)ethyl]-1,2,3,4,4a,11,12,12a-octahydropyrazino[2′,3′-3,4]pyrido[1,2-a]indole (2.1 g, described in Example 13), the latter compound was repeatedly liberated by partitioning between CH₂Cl₂ and 10% aq. NaOH. Attempts to crystallize the salts involved heating in methanol, acetonitrile, and in the case of dimethanesulfonate, heating in aqueous methanol. Finally, the TLC (silica gel, CHCl₃-hexane-MeOH 60:37:3, v/v) analysis of the recovered base showed two spots: the starting trans-product with $R_f$ 0.7, and the title cis-product with $R_f$ 0.55. The mixture was chromatographed, and the title compound (1.4 g) was separated, and converted to the dihydrochloride salt; mp 230°–232° C. (crystallized from methanol-acetonitrile 1:1, v/v); IR (mineral oil) 3630, 3440, 2700, and 2280 cm⁻¹; UV max (MeOH) 224, 272, and 276 nm (ε 42900), (9080), and (9430) resp.; NMR (DMSO-d₆) δ 2.35 (s, 3H), 5.30 (br s, 1H), 6.8–7.65 (m, 9H); and Anal. Calcd for $C_{23}H_{27}N_3O \cdot 2HCl$: C, 63.59% H, 6.73% N, 9.67% and Found: C, 62.63% H, 6.77% N, 9.36%.

EXAMPLE 19

(4a,12a-cis)-7-Bromo-1,4-diethyl-5-methyl-1,2,3,4,4a,11,12,12a-octahydropyrazino[2′,3′-3,4]pyrido[1,2-a]indole (Ib, R¹=7-Br, R²=Me, and R³ and R⁴=Et)

A mixture of (4a,12a-trans)-7-bromo-1,4-diethyl-5-methyl-1,2,3,4,4a,11,12,12a-octahydropyrazino[2′,3′-3,4]pyrido[1,2-a]indole (0.3 g, described in Example 12), sodium methoxide (0.3 g), and hexamethylphosphoramide (10 mL) was heated at 190° C. for 24 hr. After cooling, the resulting solution was poured into water, and extracted with diethyl ether. The combined extracts were washed with water, dried (MgSO₄), filtered and evaporated. The residual oil was purified chromatographically on a column of silica gel. Elution with methanol-chloroform (1:9, v/v) afforded 0.21 g of the title compound: mp 125° C.; NMR (CDCl₃) δ 0.89 and 1.10 (triplets, J=7.5 Hz, 6H), and 2.20 (s, 3H). The corresponding hydrochloride salt (mp 246° C.) was crystallized from acetonitrile or methanol; NMR (DMSO-d₆) δ 5.05 (br, s, 1H).

We claim:

1. A compound of the formula

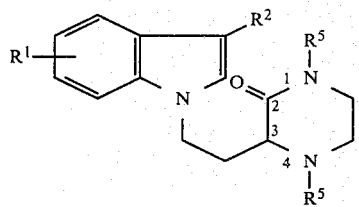

in which $R^1$ is hydrogen, halogen, lower alkyl, lower alkoxy or trifluoromethyl; $R^2$ is hydrogen or lower alkyl having one to three carbon atoms; and $R^5$ is benzyl or lower alkyl.

2. A compound of claim 1 wherein $R^1$ is hydrogen, $R^2$ is methyl and $R^5$ is lower alkyl.

3. A compound of the formula

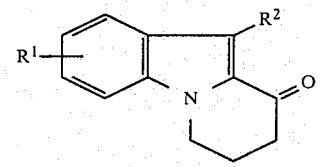

in which $R^1$ is hydrogen, halogen, lower alkyl, lower alkoxy or trifluoromethyl; and $R^2$ is hydrogen or lower alkyl having one to three carbon atoms.

4. A compound of claim 3 wherein $R^1$ is hydrogen or 2-bromo and $R^2$ is methyl.

5. A compound of the formula

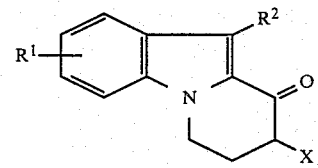

in which $R^1$ is hydrogen, halogen, lower alkyl, lower alkoxy or trifluoromethyl; $R^2$ is hydrogen or lower alkyl having one to three carbon atoms; and X is bromo or chloro.

6. A compound of claim 5 wherein $R^1$ is hydrogen or 2-bromo, $R^2$ is methyl and X is bromo.

* * * * *